United States Patent
Mais et al.

(10) Patent No.: US 6,504,059 B1
(45) Date of Patent: Jan. 7, 2003

(54) PROCESS FOR CONVERTING NITROBENZENE TO A FREE AMINOPHENOL

(75) Inventors: Franz-Josef Mais, Düsseldorf (DE); Albrecht Marhold, Leverkusen (DE); Guido Steffan, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/248,661

(22) Filed: Feb. 11, 1999

Related U.S. Application Data

(62) Division of application No. 09/008,252, filed on Jan. 16, 1998, now Pat. No. 5,900,509.

(30) Foreign Application Priority Data

Jan. 23, 1997 (DE) .......................................... 197 02 207

(51) Int. Cl.$^7$ ............................................ C07C 211/00
(52) U.S. Cl. ....................................................... 564/442
(58) Field of Search ........................................ 564/442

(56) References Cited

U.S. PATENT DOCUMENTS

| | | | |
|---|---|---|---|
| 4,307,249 A | 12/1981 | Derrenbacker | 564/418 |
| 4,518,804 A | 5/1985 | Rigterink et al. | 564/442 |
| 4,798,837 A | 1/1989 | Drabek et al. | 514/594 |
| 4,885,389 A | 12/1989 | Lee et al. | 564/418 |
| 4,980,506 A | 12/1990 | Drabek et al. | 564/442 |
| 5,107,017 A | 4/1992 | Drabek et al. | 560/358 |
| 5,132,325 A | 7/1992 | Drabek et al. | 514/594 |
| 5,153,224 A | 10/1992 | Drabek et al. | 574/594 |
| 5,288,906 A | 2/1994 | Gubelmann et al. | 564/418 |
| 5,312,991 A | 5/1994 | Miller | 564/418 |

FOREIGN PATENT DOCUMENTS

| | | | |
|---|---|---|---|
| EP | 0179022 | 4/1986 | C07C/127/22 |
| EP | 0235089 | 9/1987 | C07C/127/22 |

OTHER PUBLICATIONS

Eugen Müller: "Methoden der Organischen Chemie (Houben–Weyl) Band VI/1c Phenole Teil 1" 1996, Georg Thieme Verlag, Stuttgart, pp. 91–92.

*Primary Examiner*—Paul J. Killos
(74) *Attorney, Agent, or Firm*—Norris, McLaughlin & Marcus, P.A.

(57) ABSTRACT

Process for converting a nitrobenzene into a free aminophenol by catalytic reduction hydroxylation in the presence of an aqueous-acidic reaction medium.

7 Claims, No Drawings

PROCESS FOR CONVERTING NITROBENZENE TO A FREE AMINOPHENOL

This application is a division of application Ser. No. 09/008,252, filed Jan. 16, 1998, now U.S. Pat. No. 5,900,509 now allowed.

The present invention relates to a process for the preparation of p-haloalkoxyanilines by catalytic hydroxylation of nitrobenzenes and subsequent etherification of the resulting OH group by reaction with halogenated olefins.

p-Haloalkoxyanilines are important intermediates in the preparation of insecticidal active ingredients (see for example EP-A 179 022, DE-A 36 27 161, EP-A 221 847, EP-A 235 089 and EP-A 343 110). These anilines are usually prepared by reacting halogenated olefins with p-nitrophenol derivatives and subsequently hydrogenating the nitro group (see for example EP-A 179 022 and EP-A 235 089), by reacting halogenated olefins with N-acylated p-aminophenols and subsequently cleaving off the N-acyl group (see for example EP-A 179 022 and EP-A 235 089), by reacting the salts of p-arninophenols with halogenated olefins (see for example EP-A 179 022 and U.S. Patent Specification No. 4,518,804) or by reacting p-fluoronitrobenzene derivatives with halogenoalcohols (see for example EP-A 235 089) and subsequently hydrogenating the nitro group catalytically.

A disadvantage of these processes is the number of process steps, particularly if the preparation of the corresponding starting materials is included. Thus, for example, p-nitrophenol derivatives have to be prepared in a preliminary step by nitration of a phenol, and, following reaction with halogenated olefins, a further step is required to reduce the nitro group. It is also a great disadvantage that during the nitration, positionally isomeric compounds are also formed which have to be removed. In the case of the reaction of N-acylated aminophenols, the insertion and cleaving off of the protective group mean a markedly increased process complexity. Preparation of the aminophenol salts by nitration of a phenol and subsequent hydrogenation and salt formation is also unfavorable in view of the number of process stages and the availability of the starting materials. This is also true of the reaction of p-fluoronitroaromatic compounds with halogenoalkanols.

The object is thus to find a process for preparing p-haloalkoxyanilines which avoids multistage and lengthy reaction sequences and uses readily available starting materials.

A process for preparing p-haloalkoxyanilines of the formula (I)

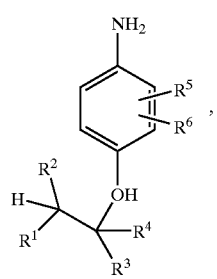

(I)

where
$R^1$ is hydrogen, halogen or $C^1$–$C_4$-halogenoalkyl and
$R^2$ to $R^6$ are, independently of one another, each hydrogen or halogen, at least one of the radicals $R^1$ to $R^4$ not being hydrogen, has now been found, which comprises converting a nitrobenzene of the formula (II)

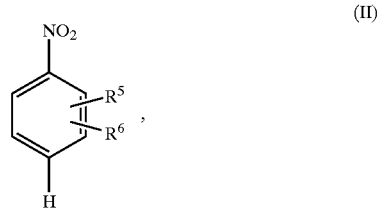

(II)

where
$R^5$ and $R^6$ are as defined for formula (I),
into a free aminophenol of the formula (III)

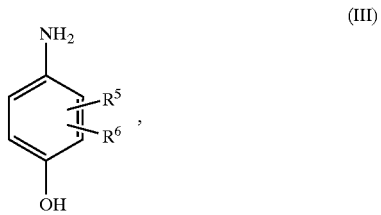

(III)

where
$R^5$ and $R^6$ are as defined for formula (I),
by catalytic reductive hydroxylation in the presence of an aqueous-acidic reaction medium, and reacting this aminophenol with a halogenated olefin of the formula (IV) or (V)

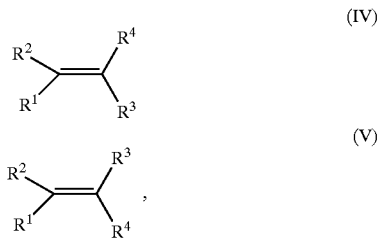

(IV)

(V)

where
$R^1$ to $R^4$ are as defined for formula (I),
in the presence of water and a catalytic amount of base.

Halogen, also in halogenoalkyl, is, for example, fluorine, chlorine or bromine.

In preferred meanings, $R^1$ is $C_1$–$C_2$-halogenoalkyl, fluorine or chlorine, $R^2$ to $R^4$ are, independently of one another, hydrogen, fluorine or chlorine, and $R^5$ and $R^6$ are, independently of one another, hydrogen, fluorine, chlorine or bromine, at least one of the radicals $R^5$ and $R^6$ not being hydrogen.

In particularly preferred meanings, $R^1$ is perfluoro-$C_1$–$C_2$-alkyl such as trifluoromethyl or pentafluoroethyl, $R^2$ to $R^4$ are, independently of one another, fluorine or chlorine, and $R^5$ and $R^6$ are, independently of one another, hydrogen or chlorine, at least one of the radicals $R^5$ and $R^6$ being chlorine.

The catalytic reductive hydroxylation can, for example, be carried out with hydrogen under pressure at elevated temperature and in the presence of catalysts.

The aqueous acidic reaction medium can be a mixture of water and a strong acid. The strong acid may be inorganic or organic. Examples include sulfuric acid, hydrochloric acid, hydrobromic acid, phosphoric acid, methanesulfonic acid and toluenesulfonic acid. Preference is given to sulfuric acid and hydrochloric acid. The concentration of the acid in the aqueous acidic reaction mixture may, for example, be from 5 to 30% by weight, preferably from 10 to 20% by weight. The amount of acid can, for example, be from 0.5 to 10 equivalents of acid per equivalent of nitrobenzene of formula (II) used. This amount is preferably from 1 to 5 equivalents, in particular 1.2 to 3 equivalents.

For example, it is possible to use from 5 to 50% by weight, preferably from 10 to 25% by weight, of a nitrobenzene of the formula (II), based on the aqueous acidic reaction medium.

It is also possible, if desired, to work in the presence of a cosolvent. The cosolvents may be water-miscible organic solvents, for example water-miscible cyclic or open-chain ethers, such as tetrahydrofuran, 1,4-dioxane, glycol monoalkyl ethers or glycol dialkyl ethers, water-miscible esters or arnides, such as ethyl acetate, N,N-dimethylformamide, N,N-dimethylacetamide or N-methylpyrrolidone, lower aliphatic carboxylic acids, such as formic acid, acetic acid or propionic acid, water-miscible ketones, such as acetone or methyl ethyl ketone, or water-miscible alcohols, such as methanol, ethanol, propanol or ethylene glycol. Preference is given to methanol, ethanol, ethylene glycol, ethylene glycol monomethyl ether, ethylene glycol dimethyl ether and 1,4-dioxane. Cosolvents may optionally be used in from 0.05 to 3 times, preferably from 0.1 to 1 times, the quantity by weight, based on the nitrobenzene of the formula (II) used.

In addition to the cosolvent, it is also possible to use a water-insoluble organic solvent in which the nitrobenzene of the formula (II) used is at least partially soluble. Examples are optionally alkyl- and/or halogen-substituted aromatic hydrocarbons, such as benzene, toluene, xylenes, chlorobenzene, dichlorobenzenes, chlorotoluenes or dichlorotoluenes. Toluene and xylenes are preferred. Water-insoluble organic solvents may optionally be used in from 0.1 to 5 times, preferably from 0.25 to 3 times, the amount by weight, based on the nitrobenzene of the formula (II) used.

It is preferred to work in the presence of a cosolvent and a water-insoluble solvent. Suitable catalysts for the catalytic reductive hydroxylation are, for example, precious metals and precious metal compounds of the platinum group elements, in particular platinum and/or palladium and/or their compounds. The catalysts may be supported on a support material. Suitable support materials are, for example, silica gels, aluminum oxides, zeolites, molecular sieves or charcoals, whose coating with precious metals or precious metal compounds can, for example, be from 0.05 to 10% by weight, preferably from 0.1 to 5% by weight. It is possible to use, for example, from 0.001 to 0.3% by weight, preferably from 0.01 to 0.1% by weight, of the catalyst (calculated as metal), based on the nitrobenzene of the formula (II) used.

The catalytic reductive hydroxylation can be carried out, for example, at temperatures of from 50 to 160° C. and pressures of from 1 to 50 bar. Preferred conditions are 60 to 130° C. and 1.2 to 20 bar.

It is advantageous to thoroughly mix the reaction mixture during the hydrogen uptake, for example by using stirrers, lifter agitators or shaker autoclaves.

The reaction mixture which is present after the catalytic reductive hydroxylation is complete can, for example, be worked up by firstly removing the catalyst, for example by filtration, then separating off and removing the organic phase, adding a base to the aqueous phase and, for example, filtering the suspension which forms at a pH of approximately 5 to 8, washing the filtration residue with water and drying it. It is also possible to initially add sufficient base to the aqueous phase that the mixture becomes strongly alkaline, and then to remove undesired byproducts by extraction with an organic solvent and then to adjust the pH to a value in the range from approximately 5 to 8. Suitable bases are, for example, hydroxides and carbonates of alkali metals and alkaline earth metals, which may also be used as aqueous solution or suspension. Sodium hydroxide and potassium hydroxide are preferred.

The free aminophenol of the formula (III) which is obtained during the catalytic reductive hydroxylation can be used directly in the second stage of the process according to the invention, the reaction with a halogenated olefin.

Suitable solvents for this reaction are polar, aprotic solvents, for example amides, sulfones, nitrites, ketones and ethers. Examples include dimethylformamide, dimethylacetamide, N-methylpyrrolidone, tetramethylenesulfone, acetonitrile, propionitrile, acetone, methyl ethyl ketone, tetrahydrofuran and 1,4-dioxane. Acetonitrile is particularly preferred.

Polar, aprotic solvents can, for example, be used in quantities of from 200 to 2000 ml, based on 1 mol of aminophenol of the formula (III). This amount is preferably from 500 to 1000 ml.

Suitable bases for the reaction of free aminophenols of the formula (III) with halogenated olefins are, for example, hydroxides, carbonates and hydrogencarbonates of alkali metals and alkaline earth metals, ammonia and organic amines. Examples include sodium carbonate, sodium hydrogencarbonate, potassium carbonate, cesium carbonate and ammonium carbonate, lithium hydroxide, sodium hydroxide, potassium hydroxide and ammonium hydroxide, triethylamine and tributylamine, pyridine, 4-dimethylaminopyridine and DBU.

Sodium carbonate, triethylamine and alkali metal hydroxides are preferred.

The base can be used, for example, in an amount which corresponds to from 1 to 50% by weight, based on the free aminophenol of the formula (III). It is also possible to meter in the base over the course of the reaction at such a rate that the pH of the reaction mixture always remains in the range from 6 to 9.5.

The reaction mixture for the reaction of a free aminophenol of the formula (III) with a halogenated olefin can, for example, contain from 0.5 to 30% by weight of water, which may be added, for example, initially and/or together with the base prior and/or continuously in small portions during the reaction.

The halogenated olefin is preferably introduced continuously or in small portions over the course of the reaction, as consumed. Progression of the reaction is evident, for example, from the pressure drop, particularly if the reaction is carried out at increased pressure.

It is preferable to introduce the base in the form of an aqueous solution and the halogenated olefin at the same time, but spatially separate, continuously or in small portions over the course of the reaction.

Suitable temperatures for the reaction of a free aminophenol of the formula (III) with a halogenated olefin are, for example, those in the range from 0 to 120° C. Preferred temperatures are from 5 to 30° C. The pressure during this reaction can, for example, be in the range from 0.5 to 5 bar. It is preferably from 1 to 2.5 bar.

p-Haloalkoxyanilines of the formula (I) are obtained in particularly good yields and purities if the process is carried out at a relatively low temperature and the base is added simultaneously with the halogenated olefin over the course of the reaction and at the rate at which the halogenated olefin is consumed.

The reaction mixture which is present following the reaction of the free aminophenol of the formula (III) with the halogenated olefin can, for example, be worked up by distillation or extraction. Distillation is preferred. The polar, aprotic solvent may be removed and optionally used again, and the prepared p-halogenoalkoxyaniline of the formula (I) can then be isolated in good yields and purities. Distillation of the product is preferably carried out under reduced pressure, for example at from 1 to 20 mbar.

The process according to the invention comprises only two reaction steps, uses readily available starting materials and is not very complex.

EXAMPLES

Example 1

An enamel autoclave was charged with 480 g of 2,5-dichloronitroberzene, 2000 g of water, 306 g of concentrated sulfuric acid, 85 g of 1,2-dimethoxyethane, 4.8 g of 5% by weight platinum-on-charcoal (approximately 60% by weight moist) and 417 g of toluene at room temperature. After the system had been rendered inert using nitrogen, hydrogen was introduced with stirring at 105° C. and from 9 to 9.5 bar. After a constant pressure had been achieved, the pressure was released and the catalyst removed by filtration while still hot. The aqueous phase was separated off whilst hot, adjusted to a pH of 12 using 50% by weight aqueous sodium hydroxide solution, extracted with 500 ml of toluene and then adjusted to a pH of 6 using concentrated hydrochloric acid. The suspension formed was filtered off at room temperature and washed with water. Drying under reduced pressure gave 273.6 g of a brownish-reddish solid which contained 98% of 2,5-dichloro-4-aminophenol. This corresponded to a yield of 60.3%.

Example 2

80 g of 2,5-dichloro-4-aminophenol dissolved in 400 ml of acetonitrile were placed in a reaction vessel fitted with stirrer, reflux condenser and inlet pipe, and then 9 ml of a saturated soda solution were added. Hexafluoropropene was then introduced into the resulting suspension, with vigorous stirring, at the rate of uptake. The reaction was slightly exothermic, as a result of which the temperature rose from 22° C. to 30° C. After 2 hours, a further 5 ml of the soda solution were added and further hexafluoropropene was introduced. After a total of 3 hours the temperature was 322° C., an almost clear solution had formed and the uptake of hexafluoropropene had ceased. The amount of hexafluoropropene consumed was 80 g. The pH of the solution was then 5. The acetonitrile was then distilled off by raising the temperature and then applying a vacuum. In the forerunnings, 380 ml of acetonitrile passed over. After a small intermediate fraction, 137 g of 2-H-hexafluoropropoxy-2,5-dichloroaniline were obtained at 145° C. and 20 mbar. The purity (determined by gas chromatography) was 97%. The principal minor component present was 1.5% of a product formed by elimination of hydrogen fluoride. The yield was 90%, based on 100% content of starting material and product.

Example 3

160 g of 2,5-dichloro-4-aminophenol dissolved in 700 ml of acetonitrile were placed in an autoclave fitted with stirrer, reflux condenser and inlet pipe, and then 10 ml of triethylamine and 10 ml of water were added. Hexafluoropropene was introduced, with vigorous stirring, in portions into the resulting mixture at 20° C. The reaction was slightly exothermic, as a result of which the temperature rose to 25° C. After 5 cycles a total of 150 g of hexafluoropropene had been added. After a total reaction time of 3 hours the reaction mixture was transferred to a distillation apparatus and the acetonitrile was distilled off by raising the temperature. In the forerunnings, 684 ml of acetonitrile passed over. After a small intermediate fraction, 275 g of 2-H-hexafluoropropoxy-2,5-dichloroaniline were obtained in the boiling range from 145 to 148° C. and at 18 mbar. The purity of the product (determined by gas chromatography) was 97.2%. The essential minor components were 2.75% of hydrogen fluoride elimination products. Accordingly, the yield was 90.3%, based on aminophenol used, and 83.8%, based on hexafluoropropene.

Example 4 (as comparison)

Example 2 was repeated but using further water instead of acetonitrile. In this way, 2-H-hexafluoropropoxy-2,5-dichloroaniline was obtained in a yield of only 10%.

What is claimed is:

1. A process for converting a nitrobenzene of the formula (II)

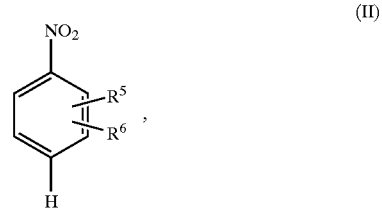

(II)

where
$R^5$ and $R^6$ independently of one another represent hydrogen or halogen,
into a free aminophenol of the formula (III)

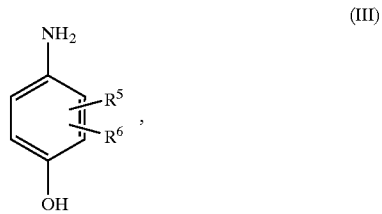

(III)

where
$R^5$ and $R^6$ are as defined for formula (II),
by catalytic reductive hydroxylation in the presence of an aqueous-acidic reaction medium, a water-miscible organic solvent as a cosolvent and a water-insoluble organic solvent.

2. A process as claimed in claim 1, wherein, $R^5$ and $R^6$, independently of one another, are hydrogen, fluorine, chlorine or bromine, at least one of the radicals $R^5$ and $R^6$ not being hydrogen.

3. A process as claimed in claim 1, wherein the aqueous acidic reaction medium comprises a mixture of water and a strong acid.

4. A process as claimed in claim 1, wherein the concentration of the acid in the aqueous acidic reaction mixture is from 5 to 30% by weight and the amount of acid is from 0.5 to 10 equivalents of acid per equivalent of nitrobenzene of the formula (II) used.

5. A process as claimed in claim 1, wherein the catalytic reductive hydroxylation is also carried out in the presence of a cosolvent which is a water-miscible organic solvent.

6. A process as claimed in claim 1, wherein the catalytic reductive hydroxylation is carried out in the presence of a cosolvent which is a water-miscible organic solvent, and also in the presence of a water-insoluble organic solvent.

7. A process as claimed in claim 1, wherein the catalytic reductive hydroxylation is carried out at from 50 to 160° C. and from 1 to 50 bar.

* * * * *